United States Patent
Ueda et al.

(10) Patent No.: US 10,835,187 B2
(45) Date of Patent: Nov. 17, 2020

(54) PHYSIOLOGICAL INFORMATION DISPLAY DEVICE, AND PHYSIOLOGICAL INFORMATION OUTPUT METHOD

(71) Applicant: Nihon Kohden Corporation, Tokyo (JP)

(72) Inventors: Yoshinori Ueda, Tokorozawa (JP); Kazumasa Ito, Tokorozawa (JP); Hideki Fujisaki, Tokorozawa (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 16/441,321

(22) Filed: Jun. 14, 2019

(65) Prior Publication Data

US 2019/0388038 A1 Dec. 26, 2019

(30) Foreign Application Priority Data

Jun. 22, 2018 (JP) ................................. 2018-118618

(51) Int. Cl.
  *G06T 11/00* (2006.01)
  *A61B 5/00* (2006.01)
  *A61B 5/1455* (2006.01)

(52) U.S. Cl.
  CPC ............ *A61B 5/742* (2013.01); *G06T 11/001* (2013.01); *A61B 5/14551* (2013.01)

(58) Field of Classification Search
  None
  See application file for complete search history.

(56) References Cited

U.S. PATENT DOCUMENTS

| | | | | |
|---|---|---|---|---|
| 4,751,502 A | * | 6/1988 | Ishii | G09G 3/3611 345/1.1 |
| 4,814,757 A | * | 3/1989 | Patterson | B60K 37/02 345/40 |
| 5,772,635 A | * | 6/1998 | Dastur | A61M 5/172 604/131 |
| 6,334,065 B1 | * | 12/2001 | Al-Ali | A61B 5/6814 600/323 |
| 2015/0150513 A1 | | 6/2015 | Kobayashi et al. | |

FOREIGN PATENT DOCUMENTS

JP 2015-107229 A 6/2015

* cited by examiner

*Primary Examiner* — Yanna Wu
(74) *Attorney, Agent, or Firm* — Sughrue Mion, PLLC

(57) ABSTRACT

A physiological information display device includes:
  a display on which a numerical value corresponding to physiological information of a subject is displayed;
  a memory that stores a program; and
  a processor that executes the program to change a number of significant digits of the numerical value that is to be displayed on the display.
In the device, the numerical value contains a first digit and a second digit, the first digit is always displayed in a first size and in a first area of the display, the number of significant digits is changed depending on whether the second digit is displayed in a second size and in a second area of the display or is not displayed, the second size being smaller than the first size, and a position and size of the first area are not changed even when the second digit is displayed.

7 Claims, 4 Drawing Sheets

PHYSIOLOGICAL INFORMATION DISPLAY DEVICE, AND PHYSIOLOGICAL INFORMATION OUTPUT METHOD

CROSS REFERENCE TO RELATED APPLICATION

This application is based on Japanese Patent Application No. 2018-118618 filed on Jun. 22, 2018, the contents of which are incorporated herein by reference.

BACKGROUND

The presently disclosed subject matter relates to a device for displaying physiological information of a subject, and also to a method for outputting the physiological information.

JP-A-2015-107229 discloses a device for displaying physiological information, In the device, sets of physiological information of various subjects are displayed as numerical values.

Usually, the number of significant digits of a numerical value which is displayed is unchanged in an almost entire numerical value range.

With respect to physiological information, the number of significant digits of a numerical value which is to be recognized by the user such as a medical person is varied depending on the condition of a subject or the numerical value range.

The present disclosed subject matter is to assist the user to accurately comprehend physiological information.

SUMMARY

A physiological information display device includes:

a display on which a numerical value corresponding to physiological information of a subject is displayed;

a memory that stores a program; and a processor configures to execute the program to change a number of significant digits of the numerical value that is to be displayed on the display.

In the device, the numerical value contains a first digit and a second digit, the first digit is always displayed in a first size and in a. first area of the display, the number of significant digits is changed depending on whether the second digit is displayed in a second size and in a second area of the display or is not displayed, the second size being smaller than the first size, and a position and size of the first area are not changed even when the second digit is displayed.

A physiological information output method includes:

acquiring physiological information of a subject;

outputting data for displaying a numerical value corresponding to the physiological information; and changing a number of significant digits of the numerical value.

In the method, the data are output so that:

a first digit of the numerical value is always displayed in a first size and in a first area;

the number of significant digits is changed depending on whether a second digit of the numerical value is displayed in a second size and in a second area or is not displayed, the second size being smaller than the first size; and a position and size of the first area are not changed even when the second digit is displayed.

According to the configuration, even when the second digit of the numerical value of the acquired physiological information is displayed, the position and size of the first area where the first digit of the numerical value is displayed are unchanged. Also in a situation where display/non-display of the second digit are frequently switched over, therefore, the visibility of the first digit can be prevented from being lowered. Moreover, the second digit is displayed in a size which is smaller than that of the first digit, and therefore the second area where the second digit is displayed can be made relatively smaller. Consequently, it is possible not only to prevent the visibility of the first digit from being lowered, but also to effectively use the display area of the display also during a period when the second digit is not displayed. As a result, it is possible to assist the user to accurately comprehend physiological information.

DETAILED DESCRIPTION OF EMBODIMENTS

Figure 1:
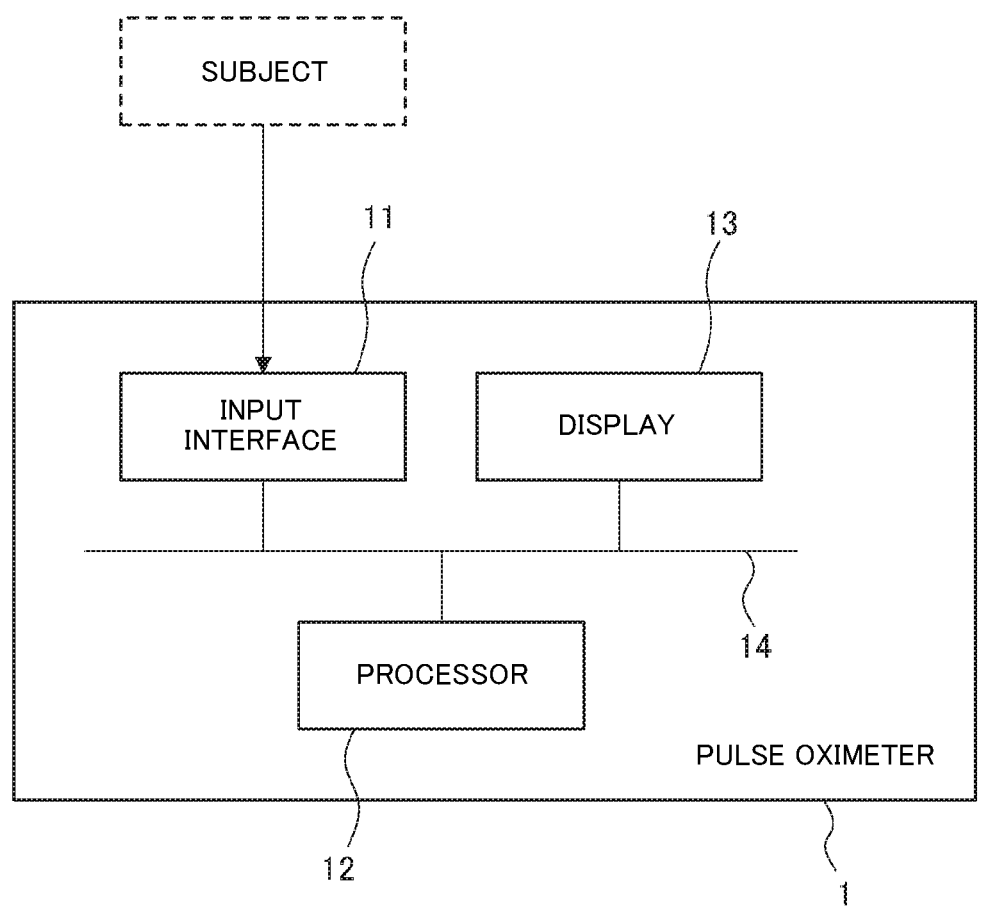
FIG. 1 illustrates the functional configuration of a pulse oximeter of an embodiment.

Hereinafter, an exemplary embodiment will be described in detail with reference to the accompanying drawings. FIG. 1 illustrates the functional configuration of a pulse oximeter 1 of the embodiment.

The pulse oximeter 1 may include one or more input interface 11, one or more processor 12, a display 13, and a bus 14. The bus 14 interconnects the input interface 11, the processor 12, and the display 13 so that signals and data can be exchanged between these components.

A probe which is not illustrated is attached to the fingertip or earlobe of a subject. The probe may include a light emitter and a light detector. The light emitter emits a red light beam and an infrared light beam. The light detector outputs a signal corresponding to the amounts of the red and infrared light beams which are transmitted through or reflected from a portion where the probe is attached. The signal is supplied to the input interface 11. The input interface 11 may include an adequate circuit configuration that converts the signal to data on which the processor 12 can execute a process that will be described later.

The processor 12 is configured to calculate at least the transcutaneous arterial oxygen saturation (SpO2) of the subject based on the data which are supplied through the input interface 11. The method for calculating the SpO2 is well known, and therefore its detailed description will be omitted. The SpO2 is an example of the physiological information, and the calculation of the SpO2 is an example of the acquisition of the physiological information.

The display 13 displays a numerical value corresponding to the calculated SpO2. Namely, the pulse oximeter 1 is an example of the physiological information display device. Specifically, the processor 12 outputs data for causing the calculated SpO2 to be displayed on the display 13 as a numerical value. The display 13 displays a numerical value based on the data supplied from the processor 12.

Figure 2C:
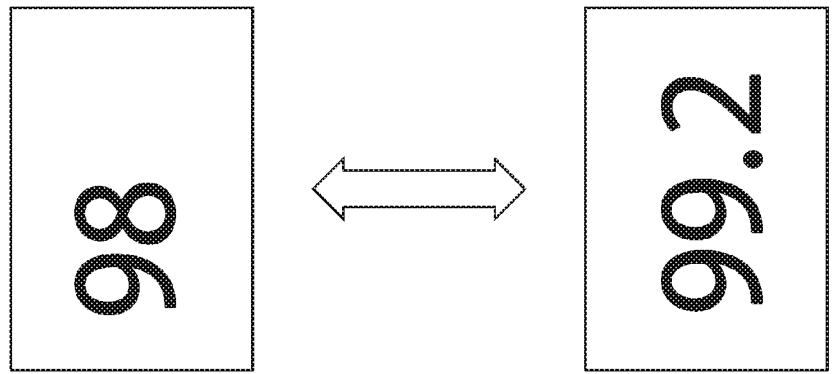
FIGS. 2A to 2C illustrate examples depicted on a display of the pulse oximeter.

The processor 12 is configured so that the number of significant digits of a numerical value which is to be displayed on the display 13 is changed in accordance with the calculated SpO2. FIG. 2A illustrates a display example of such a numerical value. A state where only the integer portion of a numerical value is displayed, and a state where the fractional portion of the numerical value is displayed in addition to the integer portion may be switched over. In other words, the number of the significant digits of the displayed numerical value is changed by causing the fractional portion of the numerical value to be displayed or not to be displayed. The integer portion of a numerical value is an example of the first digit, and the fractional portion of the numerical value is an example of the second digit.

The display 13 may include a first area 13*a* and a second area 13*b*. The integer portion of a numerical value is displayed in the first area 13*a*, The fractional portion of the numerical value is displayed in the second area 13*b*. The font size of the fractional portion of a numerical value is smaller than that of the integer portion of the numerical value. The font size of the integer portion of a numerical value is an example of the first size. The font size of the fractional portion of the numerical value is an example of the second size.

In any display state, the integer portion of a numerical value is displayed in the first area 13*a*. In other words, the integer portion of a numerical value is always displayed in the first area 13*a*. Even when the fractional portion of the numerical value is displayed in the second area 13*b*, the position and size of the first area 13*a* are not changed.

Advantages of the configuration will be described with reference to comparative examples illustrated respectively in FIGS. 2B and 2C.

Figure 2B:
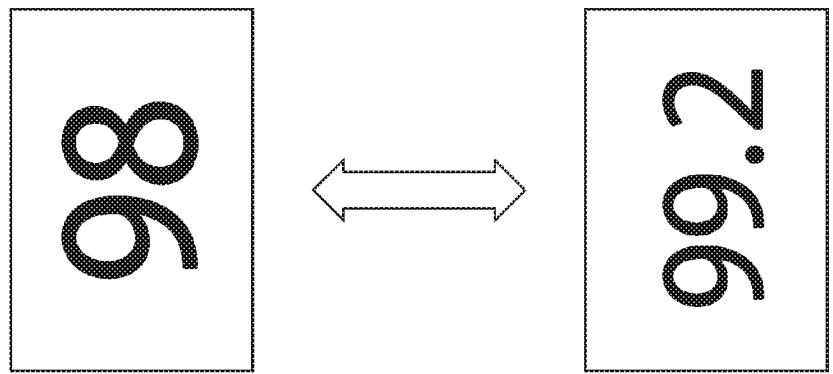
Figure 2A:
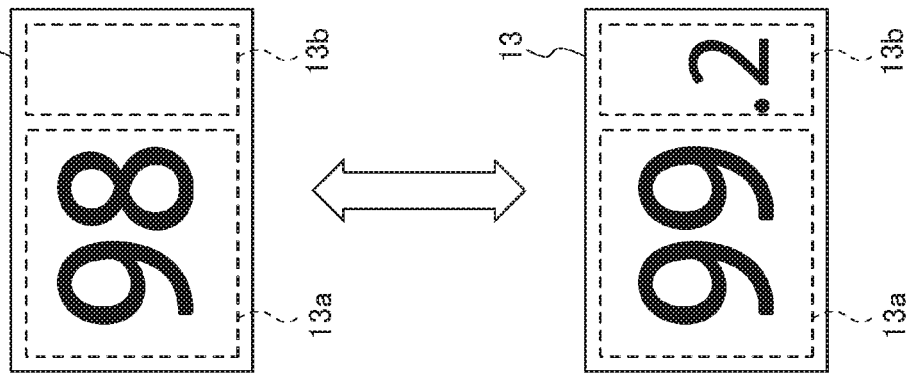

Also in the first comparative example illustrated in FIG. 2B, the number of significant digits is changed. When the fractional portion of the numerical value is displayed, however, the font size and position of the integer portion of the numerical value are changed. In this case, each time when display/non-display of the fractional portion of the numerical value are switched over, the integer portion is displaced. This is bothersome, and the visibility by the user is inevitably lowered.

Also in the second comparative example illustrated in FIG. 2C, the number of significant digits is changed. Even when the fractional portion of the numerical value is displayed, moreover, the display position of the integer portion of the numerical value is not changed. However, the font size of the integer portion coincides with that of the fractional portion. In this case, in order to ensure the display area for the fractional portion, the font size of the integer portion must be reduced, and therefore the visibility of the integer portion is lowered. Moreover, the display area for the fractional portion is relatively enlarged. During a period when the portion is not displayed, therefore, a large blank portion is produced in the display. Consequently, the display area cannot be effectively used.

As apparent from comparison with the comparative examples, even when the fractional portion of a numerical value is displayed, the position and size of the first area 13*a* where the integer portion of the numerical value is displayed are unchanged. Also in a situation where display/non-display of the fractional portion are frequently switched over, therefore, the visibility of the integer portion can be prevented from being lowered. Moreover, the font size of the fractional portion is smaller than that of the integer portion. Therefore, the second area 13*b* where the fractional portion is displayed can be made relatively smaller. Consequently, it is possible not only to prevent the visibility of the integer portion from being lowered, but also to effectively use the display area of the display 13 also during a period when the second digit is not displayed. As a result, it is possible to assist the user to accurately comprehend the value of the SpO2.

In the embodiment, in the case where the numerical value of the calculated SpO2 is within a given value range, the fractional portion of the numerical value is displayed in the second area 13*b*. In the case where the calculated SpO2 is 99% or more, specifically, the fractional portion of the numerical value is displayed in the second area 13*b*.

Figure 3:
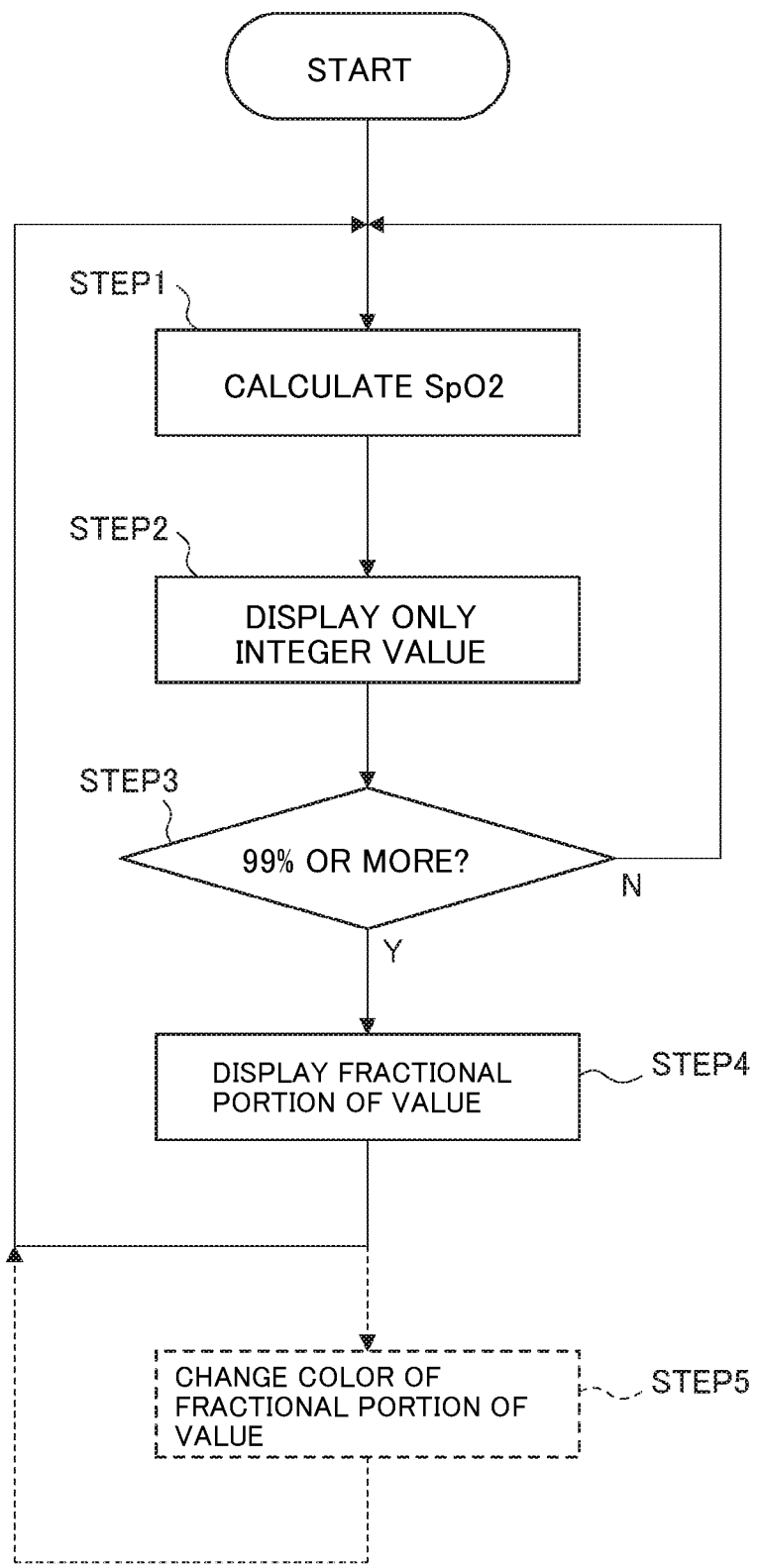
FIG. 3 illustrates an example of a process which is performed by the pulse oximeter.

FIG. 3 illustrates an operation example of the thus configured pulse oximeter 1. First, the processor 12 configured to calculate the SpO2 of the subject based on the data which are input through the input interface 11 (STEP 1).

Then, the processor 12 configured to output data for causing the integer portion of the numerical value of the calculated SpO2 to be displayed in the first area 13*a* of the display 13. As illustrated in FIG. 2A, therefore, the integer portion of the numerical value is displayed in the first area 13*a* of the display 13 (STEP 2).

Then, the processor 12 determines whether the numerical value of the calculated SpO2 is 99% or more, or not (STEP 3). If it is determined that the numerical value is smaller than 99% (N in STEP 3), the process returns to STEP 1, and the state where only the integer portion of the numerical value is displayed in the first area 13*a* is maintained until new data are input through the input interface 11.

If it is determined that the numerical value is 99% or more (Y in STEP 3), the processor 12 outputs data for causing the fractional portion of the numerical value of the calculated SpO2 to he displayed in the second area 13*b* of the display 13. As illustrated in FIG. 2A, therefore, the fractional portion of the numerical value is displayed in the second area 13*b* of the display 13 in addition to the display of the integer portion of the numerical value (STEP 4). Thereafter, the process returns to STEP 1, and the above-described process is repeated.

Figure 4:
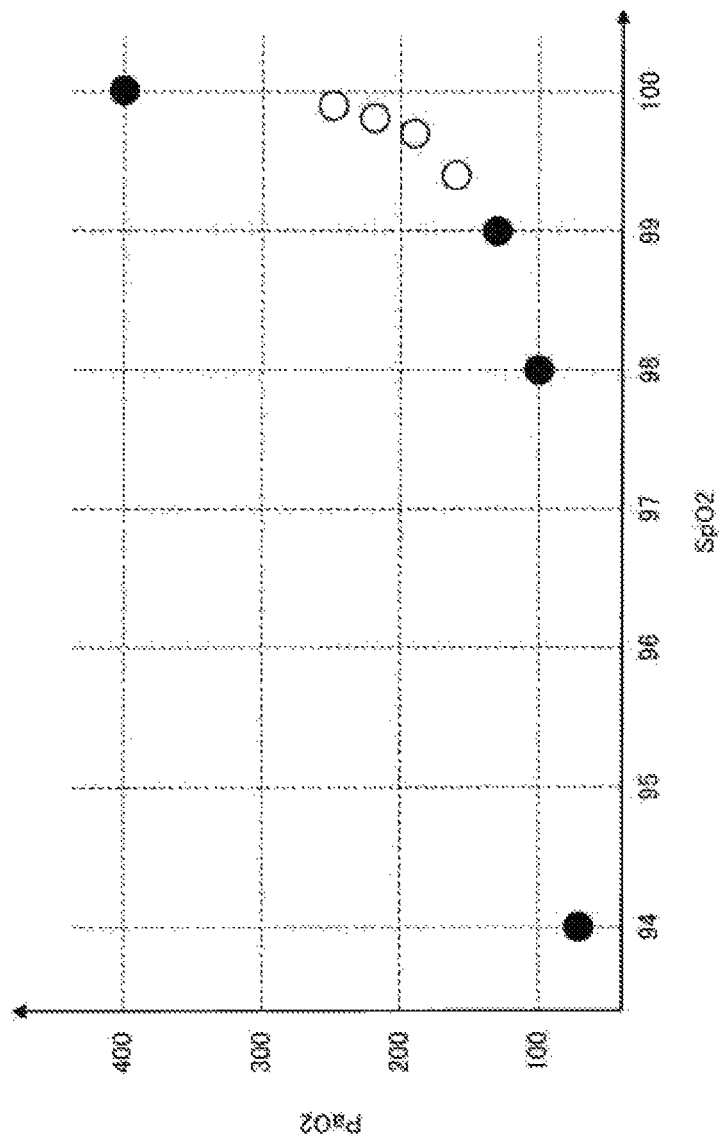
FIG. 4 illustrates a relationship between the transcutaneous arterial oxygen saturation (SpO2) and the arterial oxygen partial pressure (PaO2)

Referring to FIG. 4, advantages of the configuration in which, in the case where the numerical value of the calculated SpO2 is 99% or more, the number of significant digits of the numerical value to be displayed is increased will be described.

FIG. 4 illustrates a relationship between the transcutaneous arterial oxygen saturation (SpO2) and the arterial oxygen partial pressure (PaO2). The parameter which more accurately reflects the condition of the subject is the PaO2. However, the acquisition of the parameter involves an invasive measurement. Therefore, a medical person guesses the value of the PaO2 through the confirmation of the value of the SpO2.

However, as seen from FIG. 4, the correspondence relationship between the SpO2 and the PaO2 is non-linear. When the SpO2 exceeds 99%, moreover, the value of the PaO2 rapidly rises. In the case where only the integer portion of the value of the calculated SpO2 is displayed (in the case where only data indicated by the black circles are obtained), it is difficult to guess the value of the PaO2 which largely transits in the range from 99% to 100%.

According to the configuration, when the numerical value of the calculated SpO2 becomes 99% or more, also the fractional portion of the numerical value is displayed, and therefore data indicated by the white circles in FIG. 4 are displayed. Consequently, a medical person can more accurately guess the value of the PaO2 of the subject.

As indicated by the broken lines in FIG. 3, the processor 12 may change the color of the fractional portion of the numerical value which is displayed in the second area 13*b* of the display 13, in accordance with the numerical value of the calculated SpO2 (STEP 5). For example, the pulse oximeter may have a configuration in which, in the case where the subject must be managed so that the SpO2 does not reach 100%, the closer to 100% the SpO2 becomes, the closer to red color the fractional portion of the numerical value is changed.

According to the configuration, even when the accurate value of the fractional portion is not recognized, it is possible to know information such as the margin to the target value through visual recognition of the color.

The above-described function of the processor 12 may be realized by a general-purpose microprocessor which operates in cooperation with one or more memory, or by a dedicated integrated circuit such as a microcontroller, an FPGA, or an ASIC.

The above-described embodiment is a mere example for facilitating understanding of the presently disclosed subject matter. The configuration of the embodiment may be adequately changed or improved without departing from the spirit of the presently disclosed subject matter.

In the embodiment, when the numerical value of the calculated SpO2 is within the given range, the change in which the number of significant digits of a numerical value that is to be displayed on the display 13 is increased is performed. However, a change in which the number of significant digits is increased may be performed in response to an instruction input by the user.

The configuration which has been described above with reference to the embodiment can be applied to appropriate physiological information in which the number of significant digits of a numerical value that is to be recognized by the user is changed depending on the condition of the subject and the numerical value range.

What is clamed is:

1. A physiological information display device comprising:
    a display on which a numerical value corresponding to physiological information of a subject is displayed, wherein the numerical value comprises an integer value and a decimal value, the integer value is displayed in a first size and at a first position of the display, the decimal value is displayed in a second size and at a second position of the display, the second size being smaller than the first size;
    a memory that stores a program; and
    a processor configured to execute the program to change between displaying both the integer value and the decimal value on the display and displaying only the integer value on the display,
    wherein the first position and the first size of the integer value are not changed when displaying both the integer value and the decimal value on the display and displaying only the integer value on the display.

2. The physiological information display device according to claim 1, wherein, when the numerical value is within a given range, the decimal value is displayed on the display.

3. The physiological information display device according to claim 1, wherein a color of the decimal value is changed depending on the integer value.

4. A physiological information output method comprising:
    acquiring physiological information of a subject;
    displaying a numerical value corresponding to the physiological information, wherein the numerical value comprises an integer value and a decimal value, the integer value is displayed in a first size and at a first position of a display, the decimal value is displayed in a second size and at a second position of the display, the second size being smaller than the first size; and
    changing between displaying both the integer value and the decimal value on the display and displaying only the integer value on the display,
    wherein the first position and the first size of the integer value are not changed when displaying both the integer value and the decimal value on the display and displaying only the integer value on the display.

5. The method of claim 4, wherein, when the numerical value is within a given range, the decimal value is displayed.

6. The method of claim 4, wherein a color of the decimal value is changed depending on the integer value.

7. A physiological information display device comprising:
    a display on which a numerical value corresponding to physiological information of a subject is displayed, wherein the numerical value comprises a first value and a second value, the first value is displayed in a first size and at a first position of the display, the second value is displayed in a second size and at a second position of the display, the second size being smaller than the first size;
    a memory that stores a program; and
    a processor configured to execute the program to change between displaying both the first value and the second value on the display and displaying only the first value on the display,
    wherein the first position and the first size of the first value are not changed when displaying both the first value and the second value on the display and displaying only the first value on the display.

* * * * *